(12) United States Patent
Chevalier et al.

(10) Patent No.: US 6,337,077 B1
(45) Date of Patent: Jan. 8, 2002

(54) COMPOSITION WITH A CONTINUOUS AQUEOUS PHASE CONTAINING L-2-OXOTHIAZOLIDINE-4-CARBOXYLIC ACID

(75) Inventors: Veronique Chevalier, Villecresnes; Melanie Quest, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/522,106

(22) Filed: Mar. 9, 2000

(30) Foreign Application Priority Data

Mar. 19, 1999 (FR) .............................. 99 03476

(51) Int. Cl.7 ..................... A61K 7/42; A61K 31/425; A61K 7/135; A61K 7/00
(52) U.S. Cl. ..................... 424/401; 424/70.1; 424/59; 424/62; 424/63; 514/369; 514/844; 514/937
(58) Field of Search ................ 424/401, 70.1, 424/59, 62, 63; 514/369, 844, 937

(56) References Cited

U.S. PATENT DOCUMENTS 6,004,543 A * 12/1999 Galey
6,007,827 A * 12/1999 Galey et al.
6,063,389 A * 5/2000 Chevalier et al.
6,203,781 B1 * 3/2001 Chevalier et al.

* cited by examiner

*Primary Examiner*—Thurman K. Page
*Assistant Examiner*—Brian K. Seidleck
(74) *Attorney, Agent, or Firm*—Oblon, Spivak, McClelland, Maier & Neustadt, P.C.

(57) ABSTRACT

A composition containing a continuous aqueous phase comprising L-2-oxothiazolidine-4-carboxylic acid, at least one sequestering agent and at least one neutralizing agent, the said neutralizing agent being present in an amount which is sufficient to adjust the pH of the aqueous phase of the composition to a value of between 5 and 8. The combination of the sequestering agent and the neutralizing agent stabilizes the L-2-oxothiazolidine-4-carboxylic acid, in particular with respect to thermal degradation, and thus prevents yellowing of the composition and the formation of unpleasant odors.

17 Claims, No Drawings

COMPOSITION WITH A CONTINUOUS AQUEOUS PHASE CONTAINING L-2-OXOTHIAZOLIDINE-4-CARBOXYLIC ACID

BACKGROUND OF THE INVENTION

1. Field of the Invention

The present invention relates to a composition with a continuous aqueous phase containing L-2-oxothiazolidine-4-carboxylic acid.

2. Background of the Invention

L-2-oxothiazolidine-4-carboxylic acid, or procysteine, is known as a component of cosmetic or dermatological compositions intended for topical application to the skin. Such compositions can be intended for preventing hair loss or for stimulating the regrowth of hair, as described in EP 656 201. Procysteine is also known from patent FR 2 742 658 as an agent for depigmenting or bleaching human skin.

However, procysteine has a certain level of instability, in particular when it is in the presence of water. Thus, when it is introduced into a cosmetic composition, in particular a composition comprising water, its efficacy decreases over time. In addition, after storage for a certain period, the composition into which it is introduced shows signs of degradation: coloration, odor, which users find unacceptable. One solution for stabilizing procysteine in water consists in combining it with a polyol, in specific amounts by weight, and in limiting the amount of water to a value of 35% by weight, and preferably less than 20% by weight, relative to the total weight of the composition.

Although these compositions do in effect make it possible to convey procysteine stably over time without any loss of efficacy of this active agent, not all users necessarily find their texture suitable and the need remains for compositions capable of containing large amounts of water, for example greater than 80% by weight, in particular in the form of oil-in-water emulsions.

Admittedly, compositions in the form of oil-in-water emulsions containing procysteine are known from EP 656 201, but the Applicant has observed that these compositions were not stable over time and led to a degradation of the procysteine, resulting in the development of a nauseating sulphureous odor and yellowing of the composition.

SUMMARY OF THE INVENTION

The Inventors have now found that the use, in combination, of a sequestering agent and a neutralizing agent in an amount which is sufficient to adjust the pH of the composition to a value of between 5 and 8 makes it possible to formulate procysteine in compositions with a continuous aqueous phase which remain stable over time and/or with the temperature.

Accordingly, the present invention provides a composition, comprising:
- a continuous aqueous phase comprising L-2-oxothiazolidine-4-carboxylic acid, at least one sequestering agent and at least one neutralizing agent, wherein the pH of the aqueous phase is 5 to 8.

The composition obtained is stable, in particular with respect to thermal degradation, and also at water contents ranging up to 97% by weight, which makes it particularly suitable for cosmetic or dermatological applications.

The present invention also provides a method of preparing the composition described above by combining water, L-2-oxothiazolidine-4-carboxylic acid, the sequestering agent and an amount of at least one neutralizing agent effective to adjust the pH of the continuous aqueous phase to 5 to 8.

The present invention also provides a composition obtained by combining water, L-2-oxothiazolidine-4-carboxylic acid, at least one sequestering agent and an amount of at least one neutralizing agent effective to adjust the pH of the composition to 5 to 8.

The present invention also provides a method of stabilizing L-2-oxothiazolidine-4-carboxylic acid in a composition containing a continuous aqueous phase, comprising incorporating into the composition at least one sequestering agent and at least one neutralizing agent, wherein the neutralizing agent being present in an amount which is sufficient to adjust the pH of the aqueous phase of the composition to a value of between 5 and 8.

The present invention also provides a method of depigmenting or bleaching the skin, body hairs and/or head hair, comprising applying the inventive composition to the skin, body hairs and/or head hair.

The present invention also provides a method of preventing hair loss and/or for stimulating regrowth of the hair, comprising applying the inventive composition to the hair.

The present invention also provides a method of preventing or treating light-induced ageing and/or environment-related stress of the skin, comprising applying the inventive composition to the skin.

The present invention also provides method of preventing or treating greasy skin, comprising applying the inventive composition to the skin.

A more complete appreciation of the invention and many of the attendant advantages thereof will be readily obtained as the same becomes better understood by reference to the following detailed description.

DETAILED DESCRIPTION OF THE INVENTION

Preferably, the composition according to the invention comprises from 0.01 to 10% by weight, preferably from 0.1 to 5% and even more preferably from 0.5 to 3% by weight, of L-2-oxothiazolidine-4-carboxylic acid relative to the total weight of the composition. These ranges include all specific values and subranges therebetween, such as 0.02, 0.05, 0.2, 1,2 and 8% by weight.

The terms "L-2-oxothiazolidine-4-carboxylic acid" or "procysteine" refer to either the acid form or the carboxylate, since, as will be readily appreciated by one skilled in the art, in an aqueous medium of pH 5 to 8 there will be at least a portion of the carboxylate form of the compound. As will be readily appreciated, the carboxylate will be ion-paired with a cation, for example from the neutralizing agent.

The neutralizing agent used in the composition according to the invention can be chosen in particular from: alkali metal hydroxides, such as sodium hydroxide and potassium hydroxide; ammonia; organic bases such as monoethanolamine, diethanolamine, triethanolamine, aminomethyl-1,3-propanediol, N-methylglucamine and basic amino acids such as arginine and lysine; and mixtures thereof. The neutralizing agent is preferably triethanolamine.

The neutralizing agent is present in an amount which is sufficient to adjust the pH of the aqueous phase of the composition to between 5 and 8, preferably between 6 and 7. To do this, a person skilled in the art can readily adjust the amount of neutralizing agent as a function of the acids, other than the L-2-oxothiazolidine-4-carboxylic acid, which may be present in the composition according to the invention and as a function of the nature of the neutralizing agent. For example, when the composition according to the invention contains no acid other than L-2-oxothiazolidine-4-carboxylic acid and when the neutralizing agent used is triethanolamine, the weight ratio of the neutralizing agent to the L-2-oxothiazolidine-4-carboxylic acid is generally between 0.7:1 and 1.3:1, better still between 0.9:1 and 1.2:1. According to one preferred embodiment of the invention, the weight ratio of the neutralizing agent to the L-2-oxothiazolidine-4-carboxylic acid is 1:1.

The sequestering agent combined with the neutralizing agent can be chosen in particular from: EDTA; EDTA salts such as the disodium and tetrasodium salts of EDTA or the dipotassium salt of EDTA; disodium cocoamphodiacetate; diethylenetriamine pentaacetic acid and its salts, such as the pentasodium salt of diethylenetriamine pentaacetic acid; the trisodium salt of nitrilotriacetic acid; ascorbic acid; trisodium citrate; etidronic acid and its salts, such as the tetrasodium salt of etidronic acid; the heptasodium salt of diethylenetriamine pentamethylene phosphonic acid; the pentasodium salt of diethylenetriamine tetramethylene phosphonic acid; ethylenediamine tetramethylene phosphonic acid and its salts, such as the pentasodium salt of ethylenediamine tetramethylene phosphonic acid; sodium glucoheptanoate; and mixtures thereof. Preferably, the sequestering agent is an EDTA salt.

The sequestering agent is present, for example, in an amount of between 0.01 and 1% by weight, preferably between 0.01 and 0.5% by weight, and better still in an amount of about 0.05% by weight, relative to the total weight of the composition. These ranges include all specific values and subranges therebetween, such as 0.02, 0.1, 0.2 and 0.8% by weight.

The composition according to the invention can be more or less fluid and can have the appearance of a white or colored cream, a milk, a lotion, a serum, a mousse or an aqueous or aqueous-alcoholic gel. It can also be in the form of an aqueous or aqueous-alcoholic stick. The composition can optionally be applied to the skin or to the hair in the form of an aerosol.

According to one preferred embodiment, the composition according to the invention is in the form of an emulsion of the oil-in-water type. This expression generally means a mixture of two immiscible liquids, one of which contains a discontinuous oily phase and the other of which forms a continuous aqueous phase in which the oily phase is dispersed. As a variant, however, the oil-in-water emulsion can consist of a dispersion of oil in an aqueous phase using spherules, it being possible for these spherules to be polymeric nanoparticles, such as nanospheres and nanocapsules, or lipid vesicles of ionic and/or nonionic type, such as those described in patent applications EP 641 557 and EP 705 593, both of which are incorporated herein by reference.

The composition according to the invention can be used as a care product and/or as a make-up product for the skin. It can also be in the form of a shampoo or a conditioner.

In all cases, the composition comprises a physiologically acceptable medium, i.e. a medium which is compatible with the skin or its superficial body growths.

When the composition is in the form of an oil-in-water emulsion, the proportion of the discontinuous fatty phase can represent from 0.5 to 70% and preferably from 20 to 50% of the total weight of the composition. These ranges include all specific values and subranges therebetween, such as 1, 2, 5, 10, 15, 25, 30, 40, 50 and 60% by weight. The oils, emulsifiers and co-emulsifiers used in the composition are chosen from those conventionally used in the field considered.

As oils which can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty substances which may also be used are fatty alcohols (cetyl alcohol), fatty acids or waxes (camauba wax, ozokerite).

As emulsifiers and co-emulsifiers, it is possible to use any surfactant which produces an oil-in-water emulsion, and, for example: fatty acid esters of sorbitan, which are optionally polyoxyalkylenated, fatty acid esters of glycerol, fatty acid esters of a polyalkylene glycol, fatty alcohols, polyoxyethylenated fatty alkyl ethers, monoglyceryl ether sulphates, alkyl ether sulphates, alkyl or alkenyl oligoglycosides, N-alkylpolyhydroxyalkylamides of fatty acids, and mixtures thereof.

The emulsifier and the co-emulsifier are present in the composition in a proportion ranging from 0.3 to 30% by weight, and preferably from 0.5 to 20% by weight, relative to the total weight of the composition. These ranges include all specific values and subranges therebetween, such as 1, 2, 5, 8, 10, 15 and 25% by weight. As a variant, the composition according to the invention can be in the form of a surfactant-free emulsion, containing a polymer such as the one available from Eastman Chemical under the name AQ38S. This specific polymer is a polyester containing 89 mol % isophthalic acid, 11 mol % sodiosulphoisophthalic acid, 78 mol % diethylene glycol and 22 mol % 1,4-cyclohexane-methanol.

As will be readily appreciated by one skilled in the art, the composition according to the invention can also contain adjuvants which are common in the cosmetics field, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants are those used conventionally in the fields considered, and, for example, from 0.01 to 20% of the total weight of the composition. This range includes all specific values and subranges therebetween, such as 0.02, 0.05, 1, 2, 5, 10 and 15% by weight. Depending on their nature, these adjuvants can be introduced into the fatty phase (when it is present), into the aqueous phase, into the lipid vesicles and/or into the nanoparticles.

Hydrophilic gelling agents which may be mentioned in particular are carboxyvinyl polymers (carbomer), acrylic copolymers such as acrylate/alkylacrylate copolymers, polyacrylamides, polysaccharides, natural gums and clays, and lipophilic gelling agents which may be mentioned are modified clays such as bentones, metal salts of fatty acids and hydrophobic silica.

Active agents which can be used in particular are vitamins, keratolytic agents and/or desquamating agents such as 5-n-octanoylsalicylic acid, UV screening agents, calmants and mixtures thereof. Other depigmenting agents can also be incorporated into the composition according to the invention, such as kojic acid or hydroquinone and its derivatives, thereby allowing these agents to be used in lower doses. Agents for preventing hair loss and/or for regrowth of the hair can also be incorporated into the composition according to the invention. In the event of incompatibility, these active agents and/or L-2-oxothiazolidine-4-carboxylic acid can be incorporated into spherules, in particular ionic or nonionic vesicles and/or nanoparticles (nanocapsules and/or nanospheres), so as to isolate them from each other in the composition. In addition, care will be taken to ensure that the active agents which may be introduced into the composition according to the invention, and their concentrations, do not modify the desired properties of the L-2-oxothiazolidine-4-carboxylic acid.

Preserving agents which may be used in particular are parabens and phenoxyethanol, but formaldehyde-donating preserving agents such as diazolidinylurea are preferably avoided.

Another aspect of the invention is also the use of at least one sequestering agent combined with at least one neutralizing agent to stabilize L-2-oxothiazolidine-4-carboxylic acid in a composition with a continuous aqueous phase, where the neutralizing agent is present in an amount which is sufficient to adjust the pH of the aqueous phase of the composition to a value of between 5 and 8.

Another aspect of the invention is a process for stabilizing L-2-oxothiazolidine-4-carboxylic acid in a composition with a continuous aqueous phase, by incorporating into the composition at least one sequestering agent and at least one neutralizing agent, when the neutralizing agent is present in an amount which is sufficient to adjust the pH of the aqueous phase of the composition to a value of between 5 and 8.

The composition according to the invention can be used, in the cosmetics field, in particular for the following purposes:

for depigmenting or bleaching the skin, body hairs and/or head hair;

for preventing hair loss and/or for stimulating the regrowth of hair;

for preventing or treating light-induced ageing and/or environment-related stress, in particular on account of the radical-scavenging properties of L-2-oxothiazolidine-4-carboxylic acid; and/or for preventing or treating greasy skin, for example in the treatment of acne.

The term "environment-related stress" is defined as all of the chemical and/or physical factors in degradation of the skin which are associated with urban life and, more specifically, with exposure of the skin to fine particles of pollutants floating in the air which are liable to trigger oxidation reactions on contact with the skin. These fine particles may be contained, for example, in tobacco smoke, exhaust gases or industrial flue gases. They may be in particular pollutants such as nitrogen oxides and active oxygen. The degradation of the state of the skin is reflected by one or more of the following symptoms: the formation of wrinkles, a reduction in the water content of the skin, the formation of squamae, a loss of radiance of the complexion, redness, etc.

Yet another aspect of the invention is also the use of the composition described above for the manufacture of a preparation intended for preventing hair loss and/or for stimulating regrowth of the hair.

EXAMPLES

Having generally described this invention, a further understanding can be obtained by reference to certain specific examples which are provided herein for purposes of illustration only and are not intended to be limiting unless otherwise specified. The percentages are given on a weight basis relative to the total weight of each constituent of the composition, unless stated otherwise.

Example 1

The composition below is prepared:

| | |
|---|---|
| Cyclohexasiloxane | 10% |
| Apricot oil | 6% |
| Glycerol | 5% |
| Aluminium salt of starch crosslinked with octenylsuccinic anhydride | 3% |
| Stearyl alcohol and ceteareth-20 | 2% |
| Methylglucose sesquistearate | 2% |
| Triethanolamine | 1.1% |
| L-2-Oxothiazolidine-4-carboxylic acid | 1% |
| Preserving agents | 0.6% |
| Xanthan gum | 0.25% |
| Disodium EDTA | 0.05% |
| Water | 69% |

The oil-in-water emulsion obtained has a pH of 6.6 and is stable for at least 2 months at the following temperatures: 4° C., 25° C., 37° C. and 45° C. No yellowing or production of odor by the composition are observed at the end of this period. In addition, the level of degradation of the procysteine, as determined by HPLC, is less than 5%.

This composition can be applied to the skin in the morning and/or evening to fade away pigmentation marks.

Example 2 (comparative)

An emulsion identical to that of Example 1 is prepared, except that it contains no neutralizer (triethanolamine).

The emulsion obtained has a pH of 2.4. After two months, it gives off a pronounced sulphureous odor at all the temperatures (4° C., 25° C., 37° C. and 45° C.). A 20% degradation of the L-2-oxothiazolidine-4-carboxylic acid is also observed for the emulsion stored for two months at 45° C.

Example 3 (comparative)

An emulsion identical to that of Example 1 is prepared, except that it contains no sequestering agent (disodium EDTA).

The emulsion has a pH of 6.6. After two months, it has a slight odor at all the temperatures (4° C., 25° C., 37° C. and 45° C.) and slight yellowing of the emulsions stored at 37° C. and 45° C. is also observed.

Example 4 (comparative)

An emulsion identical to that of Example 1 is prepared, except that it contains no neutralizing agent (triethanolamine) or sequestering agent (disodium EDTA).

The emulsion has a pH of 2.3. After two months, it has a pronounced sulphureous odor and shows yellowing at all the temperatures (4° C., 25° C., 37° C. and 45° C). A 14% degradation of the L-2-oxothiazolidine-4-carboxylic acid is also observed for the emulsion stored for two months at 45° C.

The above examples clearly illustrate the better stability of the composition according to the invention compared with compositions comprising no sequestering agent and/or neutralizing agent.

Example 5

The composition below is prepared:

| Phase A | |
|---|---|
| Stearyl alcohol | 1% |
| Mixture of glyceryl stearate and of polyethylene glycol (100 EO) | 2% |
| Cyclohexasiloxane | 10% |
| Phase B | |
| Glycerol | 5% |
| Sodium hydroxide | 0.01% |
| EDTA | 0.05% |
| Preserving agents | 0.2% |
| Water | q.s. |
| Phase C | |
| Xanthan gum | 0.2% |
| Water | 20% |
| Phase D | |
| L-2-Oxothiazolidine-4-carboxylic acid | 1% |
| Triethanolamine | 1.1% |
| Water 20% | |
| Phase E | |
| Octenylsuccinate-modified starch | 3% |
| Silica | 4% |

Phase A and Phase B are heated separately to 80° C. and Phase A is then introduced into Phase B with stirring. After cooling, Phase C is then added to the emulsion obtained, followed by Phase D and finally Phase E at about 40° C.

The emulsion obtained can be used to reduce the sheen of greasy skin.

Example 6

The composition below is prepared:

| Phase A | |
|---|---|
| Mineral oil | 10% |
| Isopropyl myristate | 2% |
| Stearic acid | 2.05% |
| Stearyl alcohol and ceteareth-20 | 0.7% |
| Glyceryl stearate | 0.5% |
| Phase B | |
| Glycerol | 2% |
| Preserving agents | 0.2% |
| Water q.s. | |
| Phase C | |
| Carbomer | 0.1% |
| Triethanolamine | 0.1% |
| Water | 15% |
| Phase D | |
| Alcohol | 10% |
| Phase E | |
| Triethanolamine | 1.2% |
| L-2-Oxothiazolidine-4-carboxylic acid | 1.0% |
| Water | 15% |

Phases A and B are heated separately to 80° C. Phase A is then added to Phase B to obtain an oil-in-water emulsion, to which are successively added Phases C, D and E.

An emulsion is obtained which is particularly suitable for protecting the skin against the harmful effects of pollution.

Obviously, numerous modifications and variations of the present invention are possible in light of the above teachings. It is therefore to be understood that within the scope of the appended claims, the invention may be practiced otherwise than as specifically described herein.

This application is based on French Patent Application Ser. No. 9903476, filed on Mar. 19, 1999, and incorporated herein by reference in its entirety.

What is claimed is:

1. A composition, comprising:
   a continuous aqueous phase comprising L-2-oxothiazolidine-4-carboxylic acid, at least one sequestering agent and at least one neutralizing agent, wherein the pH of the aqueous phase is 5 to 8.

2. The composition of claim 1, wherein the sequestering agent is selected from the group consisting of EDTA, EDTA salts, disodium cocoamphodiacetate, diethylenetriamine pentaacetic acid and salts thereof, the trisodium salt of nitrilotriacetic acid, ascorbic acid, trisodium citrate, etidronic acid and salts thereof, the heptasodium salt of diethylenetriamine pentamethylene phosphonic acid, the pentasodium salt of diethylenetriamine tetramethylene phosphonic acid, ethylenediamine tetramethylene phosphonic acid and salts thereof, sodium glucoheptanoate, and mixtures thereof.

3. The composition of claim 1, wherein the sequestering agent is selected from the group consisting of the disodium and tetrasodium salts of EDTA, the dipotassium salt of EDTA, the pentasodium salt of diethylenetriamine pentaacetic acid, the tetrasodium salt of etidronic acid, the pentasodium salt of ethylenediamine tetramethylene phosphonic acid, and mixtures thereof.

4. The composition of claim 2, wherein the sequestering agent is an EDTA salt.

5. The composition of claim 1, wherein the neutralizing agent is selected from the group consisting of sodium hydroxide, potassium hydroxide, ammonia, organic bases, basic amino acids, and mixtures thereof.

6. The composition of claim 5, wherein the neutralizing agent is selected from the group consisting of monoethanolamine, diethanolamine, triethanolamine, aminomethyl-1,3-propanediol, N-methylglucamine, arginine, lysine, and mixtures thereof.

7. The composition of claim 6, wherein neutralizing agent is triethanolamine.

8. The composition of claim 1, further comprising at least one other active agent selected from the group consisting of vitamins, depigmenting agents, keratolytic agents and/or desquamating agents, calmants and UV screening agents.

9. The composition of claim 1, wherein the composition further comprises at least one oil and the composition is in the form of an oil-in-water emulsion.

10. The composition of claim 1, comprising:
   0.01 to 10% by weight of L-2-oxothiazolidine-4-carboxylic acid,
   0.01 to 1% by weight of the sequestering agent,
   wherein the weight ratio of neutralizing agent to the L-2-oxothiazolidine-4-carboxylic acid is 0.7:1 to 1.3:1.

11. A method of preparing the composition of claim 1, comprising combining water, L-2-oxothiazolidine-4-carboxylic acid, the sequestering agent and an amount of at least one neutralizing agent effective to adjust the pH of the continuous aqueous phase to 5 to 8.

12. A composition obtained by combining water, L-2-oxothiazolidine-4-carboxylic acid, at least one sequestering agent and an amount of at least one neutralizing agent effective to adjust the pH of the composition to 5 to 8.

13. A method of stabilizing L-2-oxothiazolidine-4-carboxylic acid in a composition containing a continuous aqueous phase containing said L-2-oxothiazolidine-4-carboxylic acid, comprising incorporating into the composition at least one sequestering agent and at least one neutralizing agent, wherein the neutralizing agent being present in an amount which is Sufficient to adjust the pH of the aqueous phase of the composition to a value of between 5 and 8.

14. A method of depigmenting or bleaching the skin, body hairs and/or head hair, comprising applying the composition of claim 1 to the skin, body hairs and/or head hair.

15. A method of preventing hair loss and/or for stimulating regrowth of the hair, comprising applying the composition of claim 1 to the hair.

16. A method of treating light-induced ageing and/or environment-related stress of the skin, comprising applying the composition of claim 1 to the skin.

17. A method of treating greasy skin, comprising applying the composition of claim 1 to the skin.

* * * * *

UNITED STATES PATENT AND TRADEMARK OFFICE
CERTIFICATE OF CORRECTION

PATENT NO.   : 6,337,077 B1  
DATED        : January 8, 2002  
INVENTOR(S)  : Veronique Chevalier et al.

It is certified that error appears in the above-identified patent and that said Letters Patent is hereby corrected as shown below:

<u>Column 9,</u>  
Line 14, "Sufficient" should read -- sufficient --.

This certificate supersedes Certificate of Correction issued March 19, 2002

Signed and Sealed this

Fourth Day of June, 2002

*Attest:*

*Attesting Officer*

JAMES E. ROGAN  
*Director of the United States Patent and Trademark Office*